(12) United States Patent
Moriwaki et al.

(10) Patent No.: US 7,494,680 B2
(45) Date of Patent: Feb. 24, 2009

(54) FAT OR OIL COMPOSITION

(75) Inventors: Junya Moriwaki, Tokyo (JP); Masao Shimizu, Tokyo (JP); Tsutomu Nishide, Ibaraki (JP); Shin Koike, Tokyo (JP)

(73) Assignee: Kao Corporation, Tokyo (JP)

( * ) Notice: Subject to any disclaimer, the term of this patent is extended or adjusted under 35 U.S.C. 154(b) by 716 days.

(21) Appl. No.: 10/857,020

(22) Filed: Jun. 1, 2004

(65) Prior Publication Data

US 2005/0013848 A1 Jan. 20, 2005

(30) Foreign Application Priority Data

Jun. 4, 2003 (JP) ............................. 2003-158749

(51) Int. Cl.
 A61K 47/00 (2006.01)
 A61K 31/56 (2006.01)
 A01N 37/10 (2006.01)
 A23D 7/00 (2006.01)
 C11B 5/00 (2006.01)

(52) U.S. Cl. .................. 426/601; 426/541; 424/439; 514/533; 514/786; 514/182

(58) Field of Classification Search .......... 426/601, 426/541; 514/533, 786, 182; 424/439
See application file for complete search history.

(56) References Cited

U.S. PATENT DOCUMENTS

| | | | |
|---|---|---|---|
| 4,632,840 A | | 12/1986 | Takahashi et al. |
| 5,160,759 A | | 11/1992 | Nomura et al. |
| 5,879,735 A | | 3/1999 | Cain et al. |
| 6,004,611 A | | 12/1999 | Gotoh et al. |
| 6,025,348 A | * | 2/2000 | Goto et al. ............... 514/182 |
| 6,106,879 A | | 8/2000 | Mori et al. |
| 6,258,808 B1 | | 7/2001 | Hauer et al. |
| 6,326,050 B1 | * | 12/2001 | Goto et al. ............... 426/601 |
| 2003/0054082 A1 | * | 3/2003 | Koike et al. ............. 426/601 |
| 2005/0013848 A1 | | 1/2005 | Moriwaki et al. |

FOREIGN PATENT DOCUMENTS

| | | |
|---|---|---|
| EP | 0 402 090 | 12/1990 |
| GB | 2 228 198 | 8/1990 |
| JP | 2-291228 | 12/1990 |
| JP | 3-8431 | 1/1991 |
| JP | 4-300826 | 10/1992 |
| JP | 6-220484 | 8/1994 |
| JP | 7-16051 | 1/1995 |
| JP | 7-163381 | 6/1995 |
| JP | 7-228550 | 8/1995 |
| JP | 9-52865 | 2/1997 |
| JP | 9-313133 | 12/1997 |
| JP | 10-176181 | 6/1998 |
| JP | 11-243857 | 9/1999 |
| JP | 11-299414 | 11/1999 |
| JP | 2000-290682 | 10/2000 |
| JP | 2001-220595 | 8/2001 |
| JP | 2002-112692 | 4/2002 |
| WO | WO 99/48378 | 9/1999 |

OTHER PUBLICATIONS

Enova, www.enovaoil.com, Apr. 18, 2003, p. 1-5.*
U.S. Appl. No. 11/743,997, filed May 3, 2007, Nishide, et al.

* cited by examiner

*Primary Examiner*—Johann R. Richter
*Assistant Examiner*—Abigail Fisher
(74) *Attorney, Agent, or Firm*—Oblon, Spivak, McClelland, Maier & Neustadt, P.C.

(57) ABSTRACT

Provided is a fat or oil composition containing the following components (A), (B) and (C):

(A) 100 parts by weight of a fat or oil containing from 0.1 to 10 wt. % of a monoglycerol monofatty acid ester, from 1 to 64.9 wt. % of a monoglycerol trifatty acid ester, and from 35 to 98.9 wt. % of a monoglycerol difatty acid ester having an unsaturated fatty acid content, in fatty acid components, of from 80 to 100 wt. %;

(B) from 0.1 to 3.0 parts by weight of a diglycerol fatty acid ester containing from 40 to 100% of a difatty acid ester having an unsaturated fatty acid content, in the fatty acid components, of from 70 to 100 wt. %; and (C) from 0.01 to 2 parts by weight of an antioxidant.

19 Claims, No Drawings

FAT OR OIL COMPOSITION

FIELD OF THE INVENTION

The present invention relates to a fat or oil composition having a high monoglycerol difatty acid ester content.

BACKGROUND OF THE INVENTION

Monoglycerol difatty acid esters are found to have effects of lowering accumulation of body fat and thereby preventing obesity (Japanese Patent Application Laid-Open Nos. Hei 4-300826, Hei 10-176181), effects of lowering a blood cholesterol level by using in combination with a phytosterol (International Publication No. WO99/48378) or the like. It is known that a deep frying oil containing a monoglycerol difatty acid ester has an advantage of less foaming (Japanese Patent Application Laid-Open No. Hei 11-243857). It is also known that it can be applied to an emulsion (U.S. Pat. No. 5,879,735, Japanese Patent Application Laid-Open No. Hei 3-8431). In consideration of such advantages, a fat or oil composition having a high monoglycerol difatty acid ester content has been used widely as edible oil for domestic use.

A technique capable of suppressing sputtering upon stir-frying by adding, to this monoglycerol difatty acid ester, a specific phospholipid is known (Japanese Patent Application Laid-Open No. Hei 2-291228). Also disclosed are techniques of incorporating a polyglycerol fatty acid ester and sucrose fatty acid ester in a monoglycerol difatty acid ester to improve work efficiency and facilitate cooking and to improve texture (Japanese Patent Application Laid-Open No. Hei 7-16051), a fat or oil obtained by incorporating a polyglycerol fatty acid ester in a monoglycerol difatty acid ester and suited as a confectionery material (Japanese Patent Application Laid-Open No. Hei 6-220484), and a fat or oil improved in the solubility of a phytosterol (Japanese Patent Application Laid-Open No. 2001-220595).

On the other hand, techniques of improving workability to facilitate cooking such as stir-frying or deep frying by adding a polyglycerol fatty acid ester containing a medium chain fatty acid in a fat or oil are known (Japanese Patent Application Laid-Open Nos. Hei 9-52865, 2000-290682). The fat or oil obtained by this technique however emits an odor and taste typical of the medium-chain fatty acid upon heating.

As other known techniques relating to a diglycerol fatty acid ester, there have been techniques of utilizing a diglycerol di(saturated fatty acid) ester for flour products (Japanese Patent Application Laid-Open Nos. Hei 7-228550, 2002-112692).

SUMMARY OF THE INVENTION

The present invention provides a fat or oil composition containing the following components (A), (B) and (C):

(A) 100 parts by weight of a fat or oil containing from 0.1 to 10 wt. % of a monoglycerol monofatty acid ester, from 1 to 64.9 wt. % of a monoglycerol trifatty acid ester, and from 35 to 98.9 wt. % of a monoglycerol difatty acid ester having an unsaturated fatty acid content, in fatty acid components, of from 80 to 100 wt. %;

(B) from 0.1 to 3.0 parts by weight of a diglycerol fatty acid ester containing from 40 to 100% of a difatty acid ester having an unsaturated fatty acid content, in the fatty acid components, of from 70 to 100 wt. %; and (C) from 0.01 to 2 parts by weight of an antioxidant.

DETAILED DESCRIPTION OF THE INVENTION

Monoglycerol difatty acid esters are known to have an excellent function useful for health. Compared with the conventional fats or oils (monoglycerol trifatty acid esters), monoglycerol difatty acid esters are not greasy but so light and do not always have a strong body. It seems that their taste sometimes lacks a sense of unity.

The present invention is to provide a fat or oil composition having a high monoglycerol difatty acid ester content. One of the effects of an embodiment of the invention is a good taste with a sense of unity, which is not so light, and has strong body. Another effect of an embodiment of the invention is good distribution around the food ingredients. According to an embodiment of the present invention, it also has benefits, for example, such as excellent texture, appearance, workability to permit easy cooking therewith, emulsifiability, and a unique function useful for health.

The present inventors have carried out an investigation on the cause of the above-described phenomenon and considered that the above-described phenomenon occurs as a peculiar structure attributable to the number of acyl groups of the monoglycerol difatty acid esters smaller than that of the conventional fats or oils (monoglycerol trifatty acid esters).

As a result, it has been found that a fat or oil composition which is not so light, has a strong body and has an excellent taste with a sense of unity is obtainable by using a monoglycerol difatty acid ester and a specific diglycerol fatty acid ester. It has also been found that the fat or oil composition, when used for cooking of various foods, distributes well around the food ingredients, texture, appearance, workability to permit easy cooking with the composition and emulsifiability, leading to the completion of the present invention.

The fat or oil to be used as Component (A) in the fat or oil composition of the present invention preferably contains a monoglycerol difatty acid ester (DG) in an amount of from 35 to 98.9 wt. % (which will hereinafter be described as % simply), more preferably from 51 to 98.9%, even more preferably from 70 to 97%, still more preferably from 80 to 95% from the viewpoints of physiological effects, industrial productivity and appearance.

The monoglycerol difatty acid ester is from 80 to 100%, preferably from 90 to 100%, more preferably from 93 to 98%, even more preferably from 94 to 98% of a constitutive fatty acid as an unsaturated fatty acid from the viewpoints of low-temperature resistance, appearance and physiological effects. The number of carbon atoms of the fatty acid components is preferably from 14 to 24, more preferably from 16 to 22 from the viewpoints of low-temperature resistance, appearance and physiological effects.

In the present invention, the constitutive fatty acid is the esterified fatty acid with a hydroxy group of monoglycerol or polyglycerol.

In the fatty acid components of the monoglycerol difatty acid ester, an oleic acid (C18:1) content is preferably from 20 to 70%, more preferably from 25 to 65%, even more preferably from 30 to 60%, still more preferably from 30 to 50% from the viewpoints of appearance and intake balance of fatty acids. A monoglycerol dioleate ester content is preferably less than 45%, more preferably from 0 to 40% from the viewpoint of physiological effects.

In the fatty acid components of the monoglycerol difatty acid ester, a linoleic acid (C18:2) content is preferably from 15 to 65%, more preferably from 20 to 60%, even more preferably from 30 to 55%, still more preferably from 35 to 50% from the viewpoints of appearance and intake balance of fatty acids. Moreover, a linoleic acid and oleic acid are preferably contained at a linoleic acid/oleic acid weight ratio ranging from 0.01 to 2.0, more preferably from 0.1 to 1.8, even more preferably from 0.3 to 1.7 from the viewpoints of oxidation stability and physiological effects.

In the fatty acid components of the monoglycerol difatty acid ester, a linolenic acid (C18:3) content is preferably less than 15%, more preferably from 0 to 13%, even more preferably from 0.1 to 11%, still more preferably from 2 to 9%, from the viewpoints of the appearance, intake balance of fatty acids and oxidation stability. As the isomers of linolenic acid, α-linolenic acid (C18:3, ω3) and γ-linolenic acid (C18:3, ω6) are known, with α-linolenic acid being preferred.

In the fatty acid components of the monoglycerol difatty acid ester, a saturated fatty acid content is 20% or less. It is preferably from 0 to 10%, more preferably from 2 to 7%, even more preferably from 2 to 6% from the viewpoints of appearance, physiological effects and industrial productivity. The number of carbon atoms of the unsaturated fatty acid is preferably from 14 to 24, more preferably from 16 to 22. Palmitic acid and stearic acid are especially preferred as the saturated fatty acid. It is preferred to adjust the content of short and medium chain saturated fatty acids having 13 or less carbon atoms to not greater than 2%, more preferably 0 to 1%, substantially 0% from the viewpoints of taste and prevention of smoking.

In the fatty acid components of the monoglycerol difatty acid ester, the content of trans unsaturated fatty acids is preferably from 0 to 10%, more preferably from 0.1 to 5%, even more preferably from 0.5 to 3.5% from the viewpoints of physiological effects, appearance and industrial productivity. The remaining fatty acid components preferably have from 14 to 24 carbon atoms, even more preferably from 16 to 22 carbon atoms.

In the fatty acid components of the monoglycerol difatty acid ester, a content of ω3 unsaturated fatty acids having at least 20 carbon atoms is preferably less than 15%, more preferably from 0 to 5%, even more preferably from 0 to 1% from the viewpoints of taste, oxidative stability, appearance and intake balance of fatty acids. The content of substantially 0% is most preferred. Examples of the ω3 unsaturated fatty acids having at least 20 carbon atoms include eicosapentaenoic acid (C20:5) and docosahexanoeic acid (C22:6).

From the viewpoints of physiological effects, shelf life, industrial productivity and taste, the monoglycerol difatty acid ester contains preferably at least 50%, more preferably from 55 to 100%, even more preferably from 57 to 90%, still more preferably from 60 to 80% of 1,3-difatty acid esters.

The fat or oil used as Component (A) in the present invention preferably contains from 1 to 64.9%, preferably from 1 to 48.9%, more preferably from 2.9 to 29.9%, even more preferably from 4.9 to 19.9% of a monoglycerol trifatty acid ester (TG) from the viewpoints of physiological effects, industrial productivity and appearance.

In the fatty acid components of the monoglycerol trifatty acid ester, the content of unsaturated fatty acids having from 10 to 24 carbon atoms, preferably from 16 to 22 carbon atoms is preferably from 80 to 100%, more preferably from 90 to 100%, even more preferably from 93 to 100%, still more preferably from 93 to 98%, far more preferably from 94 to 98% from the viewpoints of physiological effects and industrial productivity.

In the fat or oil to be used as Component (A) in the present invention, the content of monoglycerol monofatty acid esters (MG) is from 0.1 to 10%, preferably from 0.1 to 5%, more preferably from 0.1 to 1.5%, even more preferably from 0.1 to 1.3% from the viewpoints of the taste, appearance, emulsifiability, prevention of smoking and industrial productivity.

The fatty acid components of the monoglycerol monofatty acid ester are preferably similar to those of the monoglycerol difatty acid ester from the viewpoint of industrial productivity.

The content of free fatty acids (or salts) (FFA) contained in the fat or oil to be used as Component (A) in the present invention is preferably reduced to 3.5% or less, more preferably from 0 to 2%, even more preferably from 0 to 1%, still more preferably from 0 to 0.5%, far preferably from 0 to 0.2% from the viewpoints of taste and prevention of smoking.

The fat or oil to be used as Component (A) in the present invention may be derived from any one of vegetable and animal fats and oils. Specific examples of raw materials include rapeseed oil, sunflower oil, corn oil, soybean oil, rice oil, safflower oil, cotton seed oil and beef tallow. It may also be derived from fractions or mixtures of these fats or oils, or fats or oils obtained by modifying the fatty acid composition of the above-described fats or oils by hydrogenation or transesterification.

The fat or oil composition to be used as Component (A) in the present invention may be prepared by esterification reaction between the fatty acids derived from the above-described fats and oils and glycerin or transesterification reaction between at least one fat or oil and glycerin. Excess monoacylglycerin produced by the reaction may be removed by molecular distillation or chromatography. These reactions may also be carried out chemically using an alkali catalyst, but reaction under enzymatically mild conditions using 1,3-selective lipase is preferred, because the fat or oil obtained by this reaction is excellent in taste and the like.

The fat or oil composition of the present invention contains from 0.1 to 3.0 parts by weight of the diglycerol fatty acid ester as Component (B), preferably from 0.2 to 2.5 parts by weight, more preferably from 0.3 to 2 parts by weight, even more preferably from 0.4 to 1.5 parts by weight, still more preferably from 0.5 to 1.2 parts by weight, far preferably from 0.5 to 0.8 part by weight based on 100 parts by weight of Component (A) in consideration of taste, texture, working efficiency to permit easy cooking with the composition, emulsifiability, good distribution around the food ingredients to which the composition is added and prevention of smoking. When the content of Component (B) is 0.1 part by weight or greater based on 100 parts by weight of Component (A), the resulting monoglycerol difatty acid ester has a good taste with a sense of unity. When it is not greater than 3.0 parts by weight, strong greasiness is little felt, so that light taste characteristic of the monoglycerol difatty acid ester survives.

Examples of the diglycerol fatty acid ester to be used as Component (B) in the present invention include monofatty acid esters, difatty acid esters, trifatty acid esters, and tetrafatty acid esters, with monofatty acid esters, difatty acid esters and trifatty acid esters being preferred. Of these, difatty acid esters are more preferred. From the viewpoints of taste, texture, appearance, workability, good distribution around the food ingredients to which the composition is added, prevention of smoking and industrial productivity, the content of the difatty acid esters in Component (B) is preferably from 40 to 100%, more preferably from 60 to 99.8%, even more preferably from 80 to 99%, still more preferably from 90 to 98%. The content of monofatty acid esters preferably ranges from 0 to 20%, more preferably from 0.1 to 20%, even more preferably from 0.5 to 15%, still more preferably from 1 to 10% from the viewpoints of taste, workability, prevention of smoking and industrial productivity. The content of trifatty acid esters preferably ranges from 0 to 40%, more preferably fro 0.1 to 35%, even more preferably from 0.5 to 30%, still more preferably from 1 to 25%, from the viewpoints of taste, workability, prevention of smoking and industrial productivity.

The fatty acids constituting the diglycerol difatty acid ester to be used as Component (B) in the present invention preferably have from 14 to 24 carbon atoms, even more preferably from 16 to 22 carbon atoms.

The diglycerol difatty acid ester is made of from 70 to 100%, more preferably from 80 to 100%, even more preferably from 85 to 99%, still more preferably from 90 to 98% of a constitutive fatty acid as an unsaturated fatty acid from the viewpoints of shelf life at low temperature, taste and texture.

The content of unsaturated fatty acids in the fatty acid components of the diglycerol fatty acid ester is from 70 to 100% from the viewpoints of shelf life at low temperature, taste and texture, preferably from 80 to 100%, more preferably from 85 to 99%, even more preferably from 90 to 98%. The content of saturated fatty acids in the fatty acid components is 30% or less, preferably from 0 to 20%, more preferably from 1 to 15%, even more preferably from 2 to 10%.

The fatty acid components contain oleic acid preferably in an amount of from 5 to 70%, more preferably from 10 to 65%, even more preferably from 20 to 60%, still more preferably from 30 to 50% from the viewpoints of taste, shelf life at low temperature and oxidative stability, while they contain linoleic acid preferably in an amount of from 10 to 65%, more preferably from 15 to 60%, even more preferably from 20 to 55%, still more preferably from 25 to 50% from the viewpoints of taste, shelf life at low temperature and oxidative stability.

The content of short and medium chain saturated fatty acids having 13 or less carbon atoms in the fatty acid components is preferably 2% or less, with from 0 to 1%, substantially 0% being more preferred from the viewpoints of taste, free of oil odor and prevention of smoking. In consideration of industrial productivity, the fatty acid composition similar to that of the monoglycerol difatty acid ester is preferred.

As a raw material diglycerin for the preparation of Component (B), that obtained by adding a catalyst such as sodium hydroxide to glycerin, heating the mixture and then subjecting the reaction mixture to dehydration and condensation reaction; and that collected from a distillation residue upon preparation of glycerin. There are two types of diglycerin, that is, linear diglycerin and branched diglycerin. The former one is preferred. These diglycerin are preferably purified by steam deodorization, treatment using an adsorbent such as activated charcoal, purification through an ion exchange resin or the like are preferably employed.

As the raw material fatty acids for the preparation of Component (B), fatty acids derived from edible fats or oils may be used. Examples of the fatty acids having from 14 to 24 carbon atoms include olive oil, rice oil, sesame oil, safflower oil, soybean oil, rapeseed oil, camellia oil, corn oil, palm oil, sunflower oil, cotton seed oil, lard and beef tallow; and fractions thereof, concentrates of a specific fatty acid by distillation and the like. As these fatty acids, those purified by bleaching, deodorization or the like are preferably used in consideration of taste.

Diglycerol fatty acid esters may be obtained by esterifying the above-described diglycerin and fatty acid. The average esterification degree is preferably from 35 to 70%, more preferably from 37 to 65%, even more preferably from 40 to 62%, still more preferably from 45 to 60%. When the esterification degree exceeds 70%, they may not exert their effects. The diglycerol fatty acid esters having an esterification degree less than 35%, on the other hand, are not preferred because they may not exert sufficient effects and fail to provide good taste. The diglycerol fatty acid ester may be prepared, for example, by direct esterification of diglycerin and a fatty acid in the presence of a catalyst, by conversion of a fatty acid into the corresponding fatty anhydride or fatty acid chloride, followed by esterification, by forming a methyl ester from a fatty acid, followed by transesterification with diglycerin, and by esterification via an enzymatic reaction with lipase or the like. Alternatively, a reaction product prepared upon transesterification of a triacylglycerol and glycerin in the presence of a chemical catalyst may also be used.

In the present invention, the fat or oil composition also contains Component (C). Component (C) is an antioxidant. When Component (B) exists, not only does the oil solubility of Component (C) increase, but also an oil odor upon heating may be prevented markedly by the synergistic effect of Component (C) and Component (B).

The content of an antioxidant is preferably from 0.01 to 2 parts by weight, more preferably from 0.04 to 1 part by weight, even more preferably from 0.08 to 0.5 part by weight, still more preferably from 0.1 to 0.3 part by weight, based on 100 parts by weight of Component (A), in consideration of oxidative stability, coloration and oil odor. The antioxidant is preferably added to give an induction time of 3.0 hours or greater, more preferably from 3.5 to 20 hours, even more preferably from 4.0 to 15 hours, still more preferably from 5.0 to 10 hours in accordance with CDM test method (2.5.1.2-1996) specified in "Standard Analytical Methods for Oils and Fats" (by Oil Chemists' Society, Japan). The term "induction time" as used herein means the time (hr) up to a turning point at which the conductivity of water shows a drastic change when clean air is fed to a fat or oil sample while heating at 120° C. and a volatile substance generated by oxidation is collected in water.

Any antioxidants which may be commonly used for food may be added. Examples include vitamin E, butylhydroxytoluene (BHT), butylhydroxyanisole (BHA), tert-butylhydroquinone (TBHQ), vitamin C or derivatives thereof, and natural extracts such as rosemary extract. Of these, vitamin E, and vitamin C or derivatives thereof are preferred, with use of them in combination being more preferred.

As the vitamin E, α-, β-, γ- or δ-tocopherol, or a mixture thereof may be used. From the viewpoint of oxidation stability, δ-tocopherol is preferred. Examples of commercially available vitamin E include "E-MIX D" and "E-MIX 80" (products of Eisai), "MDE-6000" (product of Yashiro), and "E-Oil 400" (product of Riken Vitamin).

The content of vitamin E in the present invention is preferably from 0.01 to 0.5 part by weight, more preferably from 0.02 to 0.4 part by weight, even more preferably from 0.05 to 0.3 part by weight, still more preferably from 0.1 to 0.2 part by weight, each in terms of tocopherol, based on 100 parts by weight of Component (A).

As vitamin C or derivatives thereof, those soluble in monoglycerol-difatty-acid-ester-containing fat or oil are preferred. Higher fatty acid esters such as those having a $C_{12-22}$ acyl group are more preferred, of which L-ascorbyl palmitate and L-ascorbyl stearate are even more preferred, and L-ascorbic acid palmitate is still more preferred.

In the present invention, the content of vitamin C or derivative thereof is preferably from 0.004 to 0.1 part by weight, more preferably from 0.006 to 0.08 part by weight, even more preferably from 0.008 to 0.06 part by weight, still more preferably from 0.01 to 0.04 part by weight, each based on 100 parts by weight of Component (A).

The fat or oil composition to be used in the present invention preferably contains a phytosterol as Component (D). The phytosterol is a component having an effect of lowering cholesterol. In the present invention, Component (D) may be added to (A) at the weight ratio (D):(A) ranging from 0.0005:1 to 5:1, more preferably from 0.003:1 to 1:1, even more preferably from 0.012:1 to 0.2:1, still more preferably from 0.02:1 to 0.047:1 from the viewpoints of physiological effects, appearance and workability. Examples of the phytosterol include free phytosterols such as brassicasterol, α-sitosterol, β-sitosterol, stigmasterol, 7-stigmasterol, campesterol, brassicastanol, α-sitostanol, β-sitostanol, stigmastanol, 7-stigmastanol, campestanol, and cycloartenol, as well as esters thereof, such as fatty acid esters, ferulate esters, and cinnamate esters.

It is preferred that the fat or oil composition of the present invention further contains a crystallization inhibitor as Component (E). Examples of the crystallization inhibitor to be used in the present invention include polyol fatty acid esters such as polyglycerol ester of condensed ricinoleic acid, polyglycerol fatty acid esters, sucrose fatty acid esters, sorbitan fatty acid esters, polyoxyethylene sorbitan fatty acid esters, and propylene glycol esters of fatty acids.

As the polyol fatty acid ester, polyglycerol fatty acid esters, sucrose fatty acid esters and sorbitan fatty acid esters having an HLB value (Griffin's formula, *J. Soc. Cosmet. Chem.*, 1, 311 (1949)) not greater than 4, from 0.1 to 3 are preferred. The HLB value of Component (B) preferably exceeds 4 so that it can be clearly distinguished from the crystallization inhibitor described here.

In the present invention, the crystallization inhibitor is preferably added in an amount of from 0.01 to 2.5 parts by weight, more preferably from 0.02 to 0.5 part by weight, even more preferably from 0.05 to 0.2 part by weight based on 100 parts by weight of Component (A) from the viewpoint of improvement in shell life at low temperatures.

In the fat or oil composition of the present invention, an organic acid (salt) is preferably incorporated. Examples of the salt of the organic acid include alkali metal and alkaline earth metal salts, with sodium and calcium salts being preferred. The content of the organic acid (salt) is preferably from 0.0001 to 1 part by weight, more preferably from 0.015 to 0.7 part by weight, still more preferably from 0.015 to 0.5 part by weight, far preferably from 0.025 to 0.3 part by weight based on 100 parts by weight of Component (A) from the viewpoints of appearance and oxidation stability. The organic acid (salt) is required to have from 2 to 8, preferably from 2 to 6, more preferably from 4 to 6 carbon atoms. Of these, hydroxycarboxylic acids, dicarboxylic acids, and tricarboxylic acids, each having from 2 to 8 carbon atoms, and salts thereof and derivatives of them are preferred. Specific preferred examples of these hydroxycarboxylic acids, dicarboxylic acids and tricarboxylic acids include citric acid, succinic acid, maleic acid, oxalic acid, aconitic acid, itaconic acid, citraconic acid, tartaric acid, fumaric acid and malic acid, of which citric acid, tartaric acid and malic acid are more preferred. Examples of their derivatives include citric acid monoglyceride, citric acid diglyceride, succinic acid monoglyceride, succinic acid diglyceride, lactic acid monoglyceride and lactic acid diglyceride.

As the organic acid, extracts and crude drugs containing an organic acid may also be used. As the extracts or crude drugs, commercially available products in the form of powder or concentrate prepared by the extract from lemon, citron or plum may be used. The extract or crude drug may be incorporated so that the amount of the organic acid contained therein falls within the above-described range.

The content of a $C_{2-8}$ hydroxycarboxylic acid, dicarboxylic acid or tricarboxylic acid, or salt thereof is preferably from 0.001 to 0.01 part by weight, more preferably from 0.0012 to 0.007 part by weight, even more preferably from 0.0015 to 0.0045 part by weight, still more preferably from 0.0025 to 0.0034 part by weight based on 100 parts by weight of Component (A) from the viewpoints of appearance, oxidation stability, workability and taste.

The content of the derivative of a $C_{2-8}$ hydroxycarboxylic acid, dicarboxylic acid or tricarboxylic acid is preferably from 0.01 to 1 part by weight, more preferably from 0.05 to 0.7 part by weight, even more preferably fro 0.1 to 0.5 part by weight, still more preferably from 0.15 to 0.3 part by weight based on 100 parts by weight of Component (A) from the viewpoints of appearance, oxidation stability, workability, taste and texture.

Use of the $C_{2-8}$ hydroxycarboxylic acid, dicarboxylic acid or tricarboxylic acid, or salt thereof in combination with the derivative is especially preferred from the viewpoints of texture, appearance, oxidation stability and taste.

In the present invention, the content of an organic acid in the fat or oil composition may be measured by means of HPLC, or colorimetry employing orthonitrophenylhydrazine (ONPH). For example, a citric acid content may be measured through colorimetry as described below.

A fat or oil (20 g) heated to 60° C. is charged in a 100-mL separating funnel, followed by the addition of 5 mL of warm water of 60° C. The funnel is vigorously shaken for 2 minutes. Then, the funnel is allowed to stand for layer separation, and the lower layer is taken as a sample solution. In a 10-mL measuring flask are poured 2 mL of the sample solution, 1 mL of an ONPH solution (*1), and 1 mL of an ETC solution (*2). The flask is then hermetically sealed and heated at 40° C. for 30 minutes. A 1.5 mol/L aqueous solution (1 mL) of sodium hydroxide is added, followed by heating at 60° C. for 15 minutes. After cooling to room temperature, absorbance at 540 nm is measured. Based on the calibration curves drawn using aqueous citric acid solutions whose concentration has already been known, the content of citric acid is calculated in accordance with the following equation.

Citric acid content of fat or oil=(Amount of citric acid determined from a calibration curve)÷4

*1: ONPH solution: a solution obtained by dissolving 53.6 mg of orthonitrophenylhydrazine hydrochloride (ONPH) in 10 mL of 0.2 mol/L hydrochloric acid

*2: ETC solution: a solution obtained by dissolving 287.6 mg of 1-ethyl-3-(3-dimethylaminopropyl)-carbodiimide hydrochloride (ETC) in 10 mL of a 6% aqueous solution of pyridine.

It is preferred to incorporate silicone in the fat or oil composition of the present invention. The content of silicone is preferably at least 0.0003 part by weight, more preferably from 0.0005 to 0.001 part by weight, even more preferably from 0.001 to 0.006 part by weight based on 100 parts by weight of Component (A) from the viewpoints of defoaming property, oxidation stability, taste and the like. Examples of the silicone include products known as defoaming agents for food additive such as dimethylpolysiloxane, for example, "KS-66" (product of Shin-Etsu Chemical Co., Ltd.) and "THF-450" (product of Toshiba Silicone).

The fat or oil composition of the present invention may be prepared by adding, to the fat or oil having the above-described composition, diglycerol fatty acid ester, antioxidant and if necessary, phytosterol, silicone and organic acid (salt) and then heating and stirring the mixture as needed. An antioxidant such as vitamin C derivative or vitamin E may be added after-dissolved in a solvent such as ethanol.

The fat or oil composition thus obtained has a benefit, for example, such as good taste, texture, appearance, workability to permit easy cooking therewith, emulsifiability and good distribution around the food ingredients so that it may be used for various foods.

The fat or oil composition of the present invention may be used for fat or oil processed foods having the composition as a component of the food. Health food, functional food and specified health food which exhibit a special function and thereby promote health are examples of such fat or oil processed foods. Specific examples include bakery foods such as bread, cake, biscuit, pie, pizza crust and bakery mix, oil-in-water type emulsions such as soup, sauce, dressing, mayonnaise, coffee creamer, ice cream and whip cream, water-in-oil type emulsions such as margarine, spread and butter cream, snacks such as potato chips, confections such as chocolate, caramel, candy, and dessert, meat processed foods such as ham, sausage and hamburger steak, dairy products such as milk, cheese and yogurt, dough, enrobing fat or oil, filling fat or oil, noodles, frozen foods, boil-in-the-bag foods (retort foods), beverages and roux. The above-described fat or oil processed foods may be prepared by adding, in addition to the above-described fat or oil composition, food ingredients ordinarily employed depending on the kind of the processed foods. The amount of the fat or oil composition of the present invention to be added to the food varies depending on the kind of the food, but is usually from 0.1 to 100%, preferably from 1 to 80%.

It may also be used as a food ingredient such as cooking oil for deep frying or stir-frying. It is suited for cooking daily dishes such as croquette, tempura, cutlet, french fries, fried fish fillet, and spring rolls; snacks such as potato chips, tortilla chips, and fabricated potato foods; deep-fried cakes such as deep fried Japanese cracker; fried chicken; doughnuts; and instant noodles.

When the food contains a fat or oil derived from its food ingredients, a weight ratio of the fat or oil derived from the raw material to the fat or oil composition of the present invention is preferably from 95:5 to 1:99, more preferably from 95:5 to 5:95, even more preferably from 85:15 to 5:95, still more preferably from 40:60 to 5:95 in consideration of the convenience upon preparation of the fat or oil composition.

The fat or oil composition of the present invention may be used as an oil in water type emulsion. A weight ratio of the oil phase to the aqueous phase is from 1/99 to 90/10, preferably from 10/90 to 80/20, more preferably from 30/70 to 75/25 in terms of oil phase/aqueous phase. Incorporation of an emulsifier in an amount of from 0.01 to 5% is preferred, with from 0.05 to 3% being more preferred. Examples of the emulsifier include various proteins such as egg protein, soybean protein and milk protein, proteins separated therefrom, and (partially) decomposed products of these proteins; and sucrose fatty acid esters, sorbitan fatty acid esters, polyoxyethylene sorbitan fatty acid esters, glycerol monoesters of fatty acids, polyglycerol esters of fatty acids, polyglycerol esters of condensed ricinoleic acid, glycerol esters of organic acids and fatty acids, propylene glycol fatty acid esters and lecithin, and enzymatically decomposed products thereof. A stabilizer is preferably added in an amount of from 0 to 5%, more preferably from 0.01 to 2%. Examples of the stabilizer include polysaccharide thickeners and starches such as xanthan gum, gellan gum, guar gum, carrageenan, pectin, tragacanth gum and konjac mannan. In addition, a taste corrigent such as salt, sugar, vinegar, juice or seasoning, flavoring agents such as spice and flavor, colorant, preservative and antioxidant may be added. From the above-described food ingredients, oil-in-water type fat- or oil-containing foods such as mayonnaise, dressing, coffee whitener, ice cream, whip cream and beverage may be prepared in a conventional manner. A preffered mayonnaise composition is as follows.

|  | parts by weight |
|---|---|
| (Aqueous phase) | |
| Egg yolk (treated with phospholipase) | 15.0 |
| Vinegar (acidity: 10%) | 6.0 |
| Refined sugar | 1.0 |
| Sodium glutamate | 0.4 |
| Salt | 0.3 |
| Mustard powder | 0.2 |
| Thickener ("Xanthan gum" product of Dainippon Pharmaceutical) | 0.2 |
| Water | 6.9 |
| (Oil phase) | |
| Example invention product 1 | 69.0 |
| Polyglycerol fatty acid ester ("THL-3", product of Sakamoto Yakuhin) | 1.0 |

The above-described oil phase and aqueous phase can be prepared and subjected to preliminary emulsification in a homomixer. The emulsion becomes homogenized in a colloid mill, whereby a mayonnaise is obtained.

The fat or oil composition of the present invention may be used as a water-in-oil type emulsion. A weight ratio of the aqueous phase to the oil phase is from 85/15 to 1/99, preferably from 80/20 to 10/90, more preferably from 70/30 to 35/65 in terms of aqueous phase/oil phase. An emulsifier is preferably added in an amount of from 0.01 to 5%, more preferably from 0.05 to 3%. Examples of the emulsifier include various proteins such as egg protein, soybean protein and milk protein, proteins separated therefrom, and (partially) decomposed products of these proteins; and sucrose fatty acid esters, sorbitan fatty acid esters, polyoxyethylene sorbitan fatty acid esters, glycerol monoesters of fatty acids, polyglycerol esters of fatty acids, polyglycerol esters of condensed ricinoleic acid, glycerol esters of organic acids and fatty acids, propylene glycol fatty acid esters and lecithin, and enzymatically decomposed products thereof. In addition, a taste corrigent such as salt, sugar, vinegar, juice or seasoning, flavoring agent such as spice and flavor, stabilizer such as polysaccharide thickener and starch, colorant, preservative and antioxidant may be added. From the above-described food ingredients, water-in-oil type fat- or oil-containing foods such as margarine, fat spread and butter cream may be prepared. A preffered fat spread composition is as follows.

|  | Parts by weight |
|---|---|
| (Oil phase) | |
| Fat or oil (Example invention product 2) | 33.38 |
| Hydrogenated palm oil (IV = 2) | 4 |
| Hydrogenated soybean oil (IV = 43) | 2 |
| Monoglyceride ("T-95", product of Kao) | 0.5 |
| Lecithin | 0.5 |
| Polyglycerol ester of condensed ricinoleic acid ("CR-310", product of Sakamoto Yakuhin) | 0.5 |
| Flavor | 0.1 |
| Vitamin E | 0.02 |
| (Aqueous phase) | |
| Distilled water | 56.9 |
| Sucrose fatty acid ester ("F-160", product of Daiichi Kogyo Seiyaku) | 0.5 |
| Skim milk | 0.3 |
| Salt | 1.3 |

The above-described oil phase and aqueous phase is prepared, followed by mixing and emulsification in a homomixer. The emulsion is quenched in a conventional manner to plasticize it into a fat spread.

The fat or oil composition of the present invention exhibits excellent physiological activities such as body fat accumulation inhibitory action, visceral fat accumulation inhibitory action, body weight increase inhibitory action, serum triglyceride rise inhibitory action, insulin resistance improving action, blood sugar level increase inhibitory action, and HOMA index improving action. Owing to such excellent properties, the fat or oil composition of the present invention may be used for pharmaceuticals in the form of a capsule, tablet, granule, powder, liquid or gel. Pharmaceuticals may be prepared by adding, to the fat or oil composition, excipient, disintegrator, binder, lubricant, surfactant, alcohol, water, water-soluble polymer, sweetening agent, taste corrigent and acidifier, each ordinarily employed according to the dosage form. The amount of the fat or oil composition of the present invention to be added to a pharmaceutical may vary with its purpose or dosage form, but it is preferably added in an amount of from 0.1 to 80%, more preferably from 0.2 to 50%, even more preferably from 0.5 to 30%. As a dose, the amount from 0.2 to 50 g, in terms of the fat or oil composition, is preferably administered once or several portions a day. Administration term is preferably at least 1 month, more preferably at least 2 months and even more preferably from 3 to 12 months. A preffered soft capsule composition is as follows.

A soft capsule is manufactured by encapsulating 300 mg of the Example invention product 2 in an oval type soft capsule.

The fat or oil composition of the present invention may be used for animal feed. Examples of feed include livestock feed for cow, pig, fowl, sheep, horse and goat, feed for small animals such as rabbit, rat and mouse, feed for fishes such as eel, porgy, yellowtail and shrimp, and pet foods for dog, cat, bird and squirrel. Although the amount of the fat or oil composition of the present invention to be added to feed differs depending on the purpose of the feed, an amount of from 1 to 30% is usually added, with an amount of from 1 to 20% being especially preferred. The fat or oil composition may be used after substituting for a part or the whole of the existing fat or oil in the feed.

The feed is prepared by mixing the fat or oil composition with ordinary employed ingredients for feed such as meats, proteins, grains, bran, starch cakes, saccharides, vegetables, vitamins, and minerals.

Examples of the meat include livestock or animal meat of cow, pig, sheep (mutton or lamb), rabbit and kangaroo, byproducts or processed foods thereof (such as meat balls, meat bone meal and chicken meal obtained by rendering of the above-described feed ingredients, and fish meat of tuna, bonito, pompano fish, sardine, scallop, turban shell and fish meal. Examples of the proteins include animal proteins, for example, milk protein such as whey and casein and egg protein, and vegetable proteins such as soybean protein. Examples of the grains include wheat, barley, rye, milo, and corn, those of bran include rice bran and wheat bran, and those of the starch cakes include soybean cake. The total content of the meat, proteins, grains, bran, and starch cakes is preferably from 5 to 93.9% of the feed.

Examples of the saccharides include glucose, oligosaccharide, sugar, honey, starch and molasses and their content is preferably from 5 to 80% of the feed. As the vegetables, vegetable extracts may be used and the vegetable content is preferably from 1 to 30% of the feed. Examples of the vitamins include A, $B_1$, $B_2$, D, E, niacin, pantothenic acid, and carotene and their content is preferably from 0.05 to 10% of the feed. Examples of the minerals include calcium, phosphorus, sodium, potassium, iron, magnesium and zinc and their content is preferably from 0.05 to 10% of the feed. In addition, the feed may contain commonly employed additives such as gelling agent, shape retainer, pH regulator, seasoning, antiseptic and nutrition supplement as needed.

EXAMPLES

The following examples further describe and demonstrate embodiments within the scope of the present invention. These examples are given solely for the purpose of illustration and are not to be construed as a limitation of the present invention, as many variations thereof are possible without departing from the inventor's spirit and scope.

Example 1

The following fat or oil was prepared.

(1) Fat or Oil A

By using an enzyme "Lipozyme IM" (product of Novozymes), 455 parts by weight of a soybean fatty acid whose saturated fatty acid content had been reduced by wintering, 195 parts by weight of rapeseed oil fatty acid and 107 parts by weight of glycerin were esterified at 1.3 hPa and 40° C. for 5 hours. The enzyme was then filtered off. The residue was subjected to thin-film distillation at 235° C. to remove the distillate. The residue was decolored, followed by washing with water and deodorization at 235° C. for 2 hours, whereby the fat or oil A was obtained.

(2) Fat or Oil B

A commercially available salad oil (product of Nisshin Oillio) was used as the fat or oil B.

(3) Polyglycerol Ester Z

By using an enzyme "Lipozyme IM", 683 parts by weight of a rapeseed oil fatty acid and 317 parts by weight of polyglycerol, "polyglycerin #310" (product of Sakamoto Yakuhin Kogyo) were esterified at 1.3 hPa and 55° C. for 4 hours. The enzyme was then filtered off and the residue was subjected to thin film distillation at 235° C. to remove the distillate, whereby the polyglycerol ester Z was prepared.

The fat or oil A, fat or oil B and polyglycerol Z were each analyzed in the below-described method. The results are shown in Table 1 (fat or oil A, fat or oil B), and Table 2 (polyglycerol ester Z).

TABLE 1

| (wt. %) | Oil or fat A | Oil or fat B |
|---|---|---|
| Monoglycerol fatty acid ester composition | | |
| Trifatty acid ester | 10.4 | 98.1 |
| Difatty acid ester | 88.4 | 1.9 |
| Monofatty acid ester | 1.0 | 0 |
| Free fatty acid | 0.2 | 0 |
| Constitutive Fatty acid composition | | |
| C16:0 | 3.2 | 6.3 |
| C18:0 | 1.3 | 2.4 |
| C18:1 | 39.4 | 49.6 |
| C18:2 | 47.5 | 32.1 |
| C18:3 | 8.7 | 9.6 |

TABLE 2

| (wt. %) | Polyglycerol ester Z |
|---|---|
| Monoglycerol difatty acid ester | 31.6 |
| Monoglycerol trifatty acid ester | 8.1 |
| Diglycerol difatty acid ester | 35.8 |

TABLE 2-continued

| (wt. %) | Polyglycerol ester Z |
|---|---|
| Diglycerol trifatty acid ester | 4.8 |
| Triglycerol difatty acid ester | 15.3 |
| Tetraglycerol difatty acid ester | 4.4 |
| Constitutive Fatty acid composition | |
| C16:0 | 4.3 |
| C18:0 | 2.0 |
| C18:1 | 62.1 |
| C18:2 | 20.9 |
| C18:3 | 10.7 |

Analysis Method (1) Monoglycerol Fatty Acid Ester Composition

After 0.5 mL of a trimethylsilylating agent ("Silylating agent "TH", product of Kanto Chemical) was added to 10 mg of a sample fat or oil and hermetically sealed, the mixture was heated at 70° C. for 15 minutes. The reaction mixture was then subjected to gas chromatography (GLC) to analyze the monoglycerol fatty acid ester composition of the sample.

GLC Conditions:
Apparatus: "6890 model", product of Hewlett Packard
Column: "DB-1HT" (J&W Scientific) 7m
Column temperature: initial=80° C., final=340° C. Heating rate=10° C./min, retained for 20 minutes at 340° C.
Detector: FID, temperature=350° C.
Injecting part: split ratio (50:1), temperature=320° C.
Sample injection amount: 1 μL
Carrier gas: helium, 1.0 mL/min (2) Constitutive Fatty Acid Composition of Monoglycerol Fatty Acid Ester Analysis was performed in accordance with "Standard Analytical Methods for Oils and Fats" of Oil Chemists' Society, Japan (2.4.2.2.-1996).

(3) Composition of Polyglycerol Ester

In a similar manner to that employed for the analysis of monoglycerol fatty acid ester composition, a trimethylsilylated sample was subjected to GLC. From the results of its chromatogram, the elution time for a monoglycerol difatty acid ester was from 21 to 23 minutes, that for a diglycerol difatty acid ester was from 23.5 to 24.5 minutes, that for a triglycerol difatty acid ester was from 25 to 26 minutes, that for a tetraglycerol difatty acid ester was from 27 to 28 minutes, that for a monoglycerol trifatty acid ester was from 28 to 30 minutes, and that for a diglycerol trifatty acid ester was from 32 to 33 minutes. From a percentage of each peak area to the total peak area, the composition of the polyglycerol ester was determined.

(4) Constitutive Fatty Acid Composition of Polyglycerol Ester

Analysis was performed in accordance with "Standard Analytical Methods for Oils and Fats" of Oil Chemists' Society, Japan (2.4.2.2.-1996).

Example Invention Products 1 and 2, and Comparative Products 1 to 5

To the fat or oil A were added polyglycerol ester Z, antioxidant, citric acid and phytosterol to prepare Example invention products 1 and 2, and Comparative products 1 to 4. The fat or oil B was used as Comparative product 5. Their composition and induction time of CDM test method are shown in Table 3.

TABLE 3

| (parts by weight) | Example invention product | | Comparative product | | | | |
|---|---|---|---|---|---|---|---|
| | 1 | 2 | 1 | 2 | 3 | 4 | 5 |
| Fat or oil A | 100 | 100 | 100 | 100 | 100 | 100 | 0 |
| Fat or oil B | 0 | 0 | 0 | 0 | 0 | 0 | 100 |
| Polyglycerol ester | | | | | | | |
| Diglycerol difatty acid ester # | 1.0 | 1.0 | 0 | 0.04 | 3.0 | 1.0 | 0 |
| Diglycerol trifatty acid ester | 0.1 | 0.1 | 0 | 0 | 0.3 | 0.1 | 0 |
| Triglycerol difatty acid ester | 0.4 | 0.4 | 0 | 0.02 | 1.3 | 0.4 | 0 |
| Tetraglycerol difatty acid ester | 0.1 | 0.1 | 0 | 0 | 0.4 | 0.1 | 0 |
| Antioxidant | | | | | | | |
| Amount of Vitamin E *1 | 0.2 | 0.2 | 0.2 | 0.2 | 0.2 | 0 | 0 |
| Amount of Vitamin C *2 | 0.025 | 0.025 | 0.025 | 0.025 | 0.025 | 0 | 0 |
| Content of phytosterol *3 | 0.4 | 4.2 | 0.4 | 0.4 | 0.4 | 0.4 | 0.6 |
| Amount of crystallization inhibitor*4 | 0.075 | 0.075 | 0.075 | 0.075 | 0.075 | 0 | 0 |
| Organic carboxylic acids | | | | | | | |
| Amount of citric acid *5 | 0.002 | 0.002 | 0.002 | 0.002 | 0.002 | 0 | 0 |
| Amount of succinic acid monoglyceride *6 | 0.25 | 0.25 | 0.25 | 0.25 | 0.25 | 0 | 0 |
| Induction time (hr) of CDM test method | 6.0 | 5.9 | 5.9 | 5.8 | 5.5 | 2.7 | 3.8 |

; The content of difatty acid ester in diglycerol fatty acid ester = 90.9 wt. %
*1: "E-oil 600" product of Riken Vitamin (added to Example invention products 1 and 2, and Comparative products 1 to 3)
*2: "Vitamin C palmitate" product of Roche (added to Example invention products 1 and 2, and Comparative products 1 to 3)
*3: "Phytosterol" product of ADM (added to Example invention product 2)
*4: "Sunsoft QMP-5" product of Taiyo Kagaku (added to Example invention products 1 and 2, and Comparative products 1 to 3)
*5: "Citric acid" product of ADM (added to Example invention products 1 and 2, and Comparative products 1 to 3)
*6: "Sunsoft 681Nu" product of Taiyo Kagaku (Example invention products 1 and 2, Comparative products 1 to 3)

Example 2

Deep Fried Shrimp

Cooking test (deep fried shrimp) was conducted using each fat or oil (Example invention products 1 and 2, Comparative products 1 to 5) prepared in Example 1 (test 1) The results are shown in Table 4.

In an iron frying pan (24 cm in diameter) was charged 400 g of the fat or oil, followed by heating to 180° C. on an electromagnetic cooker. The odor of the fat or oil emitted upon heating was organoleptically evaluated by 3 expert panelists. Then, frozen crumb-coated shrimps (product of Katokichi), 3 shrimps per oil or fat, were deep fried at 180° C. for 2 minutes. The taste, texture and appearance of the deep fried shrimps thus obtained were organoleptically evaluated by 3 expert panelists in accordance with the below-described criteria.

The fat or oil used in the test 1 was put into an oil pot and allowed to stand still at room temperature for 1 week. A similar test was then performed again and the odor upon heating, and taste, texture and appearance of the deep fried shrimps were evaluated (test 2). The results are shown in Table 4.

Odor Upon Heating
  A: Mild feeling with weak odor emission upon heating.
  B: Less mild feeling with odor emission upon heating.
  C: Stimulating with strong odor emission upon heating.

Taste (Deep Fried Shrimp)
  A: It is not oily, is not so light and has strong body and a sense of unity.
  B: It is not oily, but light and poor in body and sense of unity.
  C: It is oily and heavy, and has a strong body and sense of unity.

Texture (Deep Fried Shrimp)
  A: The bread crumbs are crispy and the shrimp is juicy.
  B: The bread crumbs are relatively crispy and the shrimp is relatively juicy.
  C: The bread crumbs are not so crispy and the shrimp is not juicy.

Appearance (Deep Fried Shrimp)
  A: The fat or oil is drained off well and many of the bread crumbs stand vertically.
  B: The fat or oil is drained off well and some of the bread crumbs stand vertically.
  C: The fat or oil is not drained off well and few bread crumbs stand vertically.

TABLE 4

| Test | Deep fried shrimp | Example invention product 1 | Example invention product 2 | Comparative product 1 | Comparative product 2 | Comparative product 3 | Comparative product 4 | Comparative product 5 |
|---|---|---|---|---|---|---|---|---|
| 1 | Odor upon heating | A | A | B | B | B | B | B |
|   | Taste | A | A | B | B | C | A | C |
|   | Texture | A | A | B | B | A | A | C |
|   | Appearance | A | A | B | B | A | A | C |
| 2 | Odor upon heating | A | A | B | B | B | C | B |
|   | Taste | A | A | B | B | C | C | C |
|   | Texture | A | A | B | B | A | A | C |
|   | Appearance | A | A | B | B | A | A | C |

Even after repeated use, odor of the Example invention products upon heating was weak and they had good workability to permit easy cooking therewith. The appearance and texture of the bread crumbs and texture of the shrimp deep-fried using the example products were each excellent. The taste of the deep fried shrimp was not so light and had a strong body so that it was totally excellent. The fat or oil according to the present invention was sufficiently suited for use as a cooking oil.

Example 3

Stir-Fried Rice

Cooking test (stir-fried rice) was performed using each oil or fat (Example invention product 1 and Comparative products 1 and 5) prepared in Example 1. The results are shown in Table 5.

In an iron frying pan (24 cm in diameter) was poured 10 g of the fat or oil, followed by heating for 30 seconds on a gas heater (at high heat). In the frying pan was charged 200 g of cold cooked rice, followed by heating for 1 minute and 15 seconds while breaking up the rice into individual grains. The rice was then added with 5 g of soy sauce and heated further for 15 seconds. The taste, texture and appearance of the resulting stir-fried rice were organoleptically evaluated by 3 expert panelists in accordance with the below-described criteria:

Taste (Stir-Fried Rice)
  A: It is not oily, is not so light and has a strong body and sense of unity
  B: It is not oily, light and poor in body and sense of unity.
  C: It is oily and heavy and has a strong body and sense of unity.

Texture (Stir-Fried Rice)
  A: Rice is not sticky.
  B: Rice is relatively sticky.
  C: Rice is sticky.

Appearance (Stir-Fried Rice)
  A: The fat or oil spreads over each grain so uniformly that the rice grains are separated well and have luster.
  B: The fat or oil does not spread over each grain uniformly, and the rice grains are neither completely separated nor has luster.
  C: The fat or oil does not spread over each grain, so that the rice grains are not separated and damaged.

TABLE 5

| Fried rice | Example invention product 1 | Comparative product 1 | Comparative product 5 |
|---|---|---|---|
| Taste | A | B | C |
| Texture | A | B | C |
| Appearance | A | B | C |

The Example invention product had good distribution around the rice grains to permit easy cooking therewith. The taste, texture and appearance of the stir-fried rice obtained using the Example Invention products were excellent, suggesting the fat or oil according to the present invention was suited for cooking use sufficiently.

Example 4

Scrambled Eggs

With each fat or oil (Example invention product 1 and Comparative products 1 and 5) prepared in Example 1, a cooking test (scrambled egg) was performed. The results are shown in Table 6.

In an iron frying pan (24 cm in diameter), 5 g of the fat or oil was poured and it was heated for 30 seconds on a gas heater (at high heat). In the frying pan, 50 g of beaten eggs was added and heated for 20 seconds while stirring. The taste, texture and appearance of the scrambled eggs thus prepared were organoleptically evaluated by 3 expert panelists in accordance with the following criteria.

Taste (Scrambled Eggs)
A: It is not oily, is not so light and has a strong body and sense of unity
B: It is not oily, light and poor in body and sense of unity.
C: It is oily and heavy and has a strong body and sense of unity.

Texture (Scrambled Eggs)
A: The egg is fluffy and juicy.
B: The egg is relatively fluffy and juicy.
C: The egg is neither fluffy nor juicy.

Appearance (Scrambled Eggs)
A: The egg and fat or oil mixes well and the scrambled eggs are not greasy.
B: The egg and fat or oil do not mix well and the scrambled eggs are a little greasy.
C: The egg and the fat or oil do not mix, so that the fat or oil stays greasy and is afloat on the surface of the scrambled eggs.

TABLE 6

|  | Example invention product | Comparative product | |
| --- | --- | --- | --- |
| Scrambled eggs | 1 | 1 | 5 |
| Taste | A | B | C |
| Texture | A | B | C |
| Appearance | A | B | C |

The Example invention product had good distribution around eggs to permit easy cooking therewith. The taste, texture and appearance of the scrambled eggs cooked using the Example invention product were excellent so that the fat or oil according to the present invention was suited for cooking use sufficiently.

Example 4

Oil-Water Separated Dressing

A cooking test (oil-water separated dressing) was performed using each fat or oil (Example invention product 1 and Comparative products 1 and 5). The results are shown in Table 7.

First, 50 mL of the fat or oil and 50 mL of an aqueous phase (non-oil dressing, product of Riken Vitamin) were charged in a glass sample bottle. After covered with a lid, the bottle was vigorously shaken 10 times by using hands. Immediately after that, the bottle was allowed to stand still and the water-oil separation degree was measured.

Then, 15 g of the dressing thus emulsified by shaking 10 times by using hands was poured over 20 g of lettuce and the taste and appearance of the salad were organoleptically evaluated by 3 expert paneists in accordance with the below-described criteria.

Taste (Lettuce Salad)
A: It is not greasy, is not so light and has a strong body and sense of unity. A taste of the lettuce does not remain.
B: It is a little greasy, light and poor in body and sense of unity. A taste of the lettuce remains.
C: It is greasy and heavy and has a strong body and sense of unity.

Appearance (Lettuce Salad)
A: Separation of the dressing hardly occurs, the dressing mixes well with the lettuce, and it hardly drops on a dish.
B: Separation of the dressing occurs at some degree. The dressing does not mix well with the lettuce and some of the dressing drops on a dish.
C: Separation of the dressing occurs. The dressing does not mix with the lettuce and it drops on a dish.

TABLE 7

|  | Example invention product | Comparative product | |
| --- | --- | --- | --- |
| Dressing | 1 | 1 | 5 |
| Separation degree of aqueous phase # Lettuce salad | 48 | 92 | 100 |
| Taste | A | B | C |
| Appearance | A | B | C |

; Separation degree of aqueous phase = Height of aqueous phase 60 seconds after shaking/Height of aqueous phase before shaking × 100

The oil-water separated dressing obtained using the Example invention product was emulsified well after shaking, so that separation of it hardly occurred. The Example invention product had good distribution around lettuce to permit a pleasant taste. The taste and appearance of the lettuce salad were excellent. As a result, the fat or oil of the present invention proved to be much suited for dressing use.

The fat or oil compositions of the present invention having high monoglycerol-difatty-acid-ester-content are excellent in effects of lowering body fat accumulation and thus preventing obesity in combination with a specific diglycerol fatty acid ester. It is suited for such as a cooking oil, because the composition is markedly improved in light feel specific to the monoglycerol difatty acid ester, has a good taste with sense of unity, and in addition is excellent in distribution around the food ingredients to which the composition is applied, and has good texture, appearance, workability and emulsifiability.

The invention claimed is:

1. A fat or oil composition comprising the following components (A), (B) and (C):
   (A) 100 parts by weight of a fat or oil comprising:
      from 0.1 to 10 wt. % of a monoglycerol monofatty acid ester,
      from 1 to 64.9 wt. % of a monoglycerol trifatty acid ester, and
      from 35 to 98.9 wt. % of a monoglycerol difatty acid ester, wherein said monoglycerol difatty acid ester is comprised of from 80 to 100 wt. % of a constitutive fatty acid as an unsaturated fatty acid;

(B) from 0.1 to 3.0 parts by weight of a diglycerol fatty acid ester comprising from 40 to 100 wt. % of a difatty acid ester, wherein said diglycerol difatty acid ester is comprised of from 70 to 100 wt. % of a constitutive fatty acid as an unsaturated fatty acid; and (C) from 0.01 to 2 parts by weight of an antioxidant.

2. The fat or oil composition of claim 1, further comprising a phytosterol as Component (D) at a weight ratio of from 0.0005:1 to 5:1 in terms of (D):(A).

3. The fat or oil composition of claim 1, further comprising a crystallization inhibitor as Component (E) in an amount of from 0.01 to 2.5 parts by weight based on 100 parts by weight of Component (A).

4. A food comprising the fat or oil composition according to claim 1.

5. A pharmaceutical comprising the fat or oil composition according to claim 1.

6. A feed comprising the fat or oil composition according to claim 1.

7. The fat or oil composition according to claim 1, wherein fatty acid components of said monoglycerol difatty acid ester comprise 20-70% of an oleic acid (C18:1).

8. The fat or oil composition according to claim 1, wherein fatty acid components of said monoglycerol difatty acid ester comprise 15 to 65% of a linoleic acid (C18:2).

9. The fat or oil composition according to claim 1, wherein fatty acid components of said monoglycerol difatty acid ester comprise less than 15% of a linolenic acid (C18:3).

10. The fat or oil composition according to claim 1, wherein fatty acid components of said monoglycerol difatty acid ester comprise less than 10% of saturated fatty acids.

11. The fat or oil composition according to claim 1, wherein fatty acid components of said monoglycerol difatty acid ester comprise 0 to 10% of trans unsaturated fatty acids.

12. The fat or oil composition according to claim 1, wherein fatty acid components of said monoglycerol difatty acid ester comprise less than 15% of $\omega 3$ unsaturated fatty acids having at least 20 carbon atoms.

13. The fat or oil composition according to claim 1, wherein monoglycerol difatty acid ester comprise at least 50% of 1,3-difatty acid ester.

14. The fat or oil composition according to claim 1, wherein said diglycerol fatty acid ester has a difatty acid ester content of from 60 to 99.8%.

15. The fat or oil composition according to claim 1, wherein said diglycerol fatty acid ester has a monofatty acid ester content of 0 to 20%.

16. The fat or oil composition according to claim 1, wherein said diglycerol fatty acid ester has a trifatty acid ester content of 0 to 40%.

17. The fat or oil composition according to claim 1, wherein said diglycerol fatty acid ester is made from 70 to 100% of constitutive fatty acids as unsaturated fatty acids.

18. The fat or oil composition according to claim 1, wherein said diglycerol fatty acid ester has an average esterification degree of from 35 to 70%.

19. The fat or oil composition according to claim 1, wherein said antioxidant is comprised of a mixture of vitamin E and Vitamin C.

* * * * *